US011744879B2

(12) United States Patent
Arce Saez et al.

(10) Patent No.: US 11,744,879 B2
(45) Date of Patent: Sep. 5, 2023

(54) RECOMBINANT FSH COMPOSITION FOR CONTROLLED OVARIAN STIMULATION

(71) Applicant: FERRING B.V., Hoofddorp (NL)

(72) Inventors: Joan-Carles Arce Saez, Parsippany, NJ (US); Lisbeth Helmgaard, Copenhagen (DK); Bjarke Mirner Klein, Copenhagen (DK)

(73) Assignee: FERRING B.V., Hoofddorp (NL)

( * ) Notice: Subject to any disclaimer, the term of this patent is extended or adjusted under 35 U.S.C. 154(b) by 1 day.

(21) Appl. No.: 16/642,777

(22) PCT Filed: Aug. 31, 2018

(86) PCT No.: PCT/EP2018/073442
§ 371 (c)(1),
(2) Date: Feb. 27, 2020

(87) PCT Pub. No.: WO2019/043143
PCT Pub. Date: Mar. 7, 2019

(65) Prior Publication Data
US 2020/0197493 A1 Jun. 25, 2020

(30) Foreign Application Priority Data
Sep. 1, 2017 (EP) .................................... 17189119

(51) Int. Cl.
*A61K 38/24* (2006.01)
*G01N 33/68* (2006.01)
*A61P 15/08* (2006.01)
*A61K 38/22* (2006.01)
*C07K 16/26* (2006.01)

(52) U.S. Cl.
CPC .............. *A61K 38/24* (2013.01); *A61K 38/22* (2013.01); *A61P 15/08* (2018.01); *G01N 33/6893* (2013.01); *C07K 16/26* (2013.01)

(58) Field of Classification Search
None
See application file for complete search history.

(56) References Cited

U.S. PATENT DOCUMENTS

| 7,964,562 | B2 | 6/2011 | Filicori |
|---|---|---|---|
| 7,985,732 | B2 | 7/2011 | Filicori |
| 8,951,967 | B2 | 2/2015 | Cottingham et al. |
| 9,320,778 | B2 | 4/2016 | Saez |
| 9,546,204 | B2 | 1/2017 | Cottingham et al. |
| 9,694,052 | B2 | 7/2017 | Arce |
| 9,771,407 | B2 | 9/2017 | Cottingham et al. |
| 10,064,920 | B2 | 9/2018 | Saez |
| 10,413,592 | B2 | 9/2019 | Arce et al. |
| 10,464,984 | B2 | 11/2019 | Plaksin et al. |
| 10,624,953 | B2 | 4/2020 | Arce |
| 10,660,938 | B2 | 5/2020 | Arce Saez et al. |
| 11,291,708 | B2 | 4/2022 | Arce |
| 11,351,228 | B2 | 6/2022 | Arce et al. |
| 11,439,686 | B2 | 9/2022 | Arce Saez et al. |
| 2004/0248784 | A1 | 12/2004 | Filicori |
| 2008/0119394 | A1 | 5/2008 | Filicori |
| 2017/0281731 | A1 | 10/2017 | Filicori |
| 2018/0079794 | A1 | 3/2018 | Cottingham et al. |
| 2018/0125942 | A1 | 5/2018 | Arce Saez et al. |
| 2019/0002518 | A1 | 1/2019 | Aharonov et al. |
| 2021/0093697 | A1 | 4/2021 | Arce et al. |
| 2021/0353717 | A1 | 11/2021 | Arce Saez et al. |
| 2022/0370567 | A1 | 11/2022 | Arce |

FOREIGN PATENT DOCUMENTS

| WO | WO-2012/168680 A1 | 12/2012 |
|---|---|---|
| WO | WO-2013/020996 A1 | 2/2013 |
| WO | WO-2016/166288 A1 | 10/2016 |
| WO | WO-2019/211153 A1 | 11/2019 |
| WO | WO-2020/079127 A1 | 4/2020 |

OTHER PUBLICATIONS

Shiko Maruyama and Sayaka Nakamura, Economics and Human Biology 18 (2015) 125-138 (Year: 2015).*
Andersen et al., Fertility and Sterility vol. 107, No. 2, Feb. 2017 0015-0282 (Year: 2017).*
Arce et al., Fertility and Sterility vol. 102, No. 6, Dec. 2014 0015-0282 (Year: 2014).*
Arce et al., Fertil Steril, 2013; 99: 1644-53 (Year: 2013).*
Ishihara et al., "A randomised, assessor-blind, AME-stratified, dose-response trial in Japanese IVF/ICSI patients undergoing controlled ovarian stimulation with follitropin delta", Abstract # P-673; p. i444, presented at the 33rd Annual Meeting of ESHRE, Geneva, Switzerland Jul. 2-5, 2017 (Year: 2017).*
Clinical Endocrinology (2015) 83, 902-912 (Year: 2015).*
Vicky et al., "Obesity adversely affects serum anti-mullerian hormone (AMH) levels in Caucasian women," Journal of Assisted Reproduction and Genetics, vol. 32. No. 9, pp. 1305-1311 (Jul. 2015).
Japanese Office Action dated May 31, 2022 in application No. 2020-182295 (based on PCT/EP2018/073442) [English Translation].
U.S. Appl. No. 17/817,274, filed Aug. 3, 2022, Ferring B.V.

* cited by examiner

*Primary Examiner* — Christina M Borgeest
(74) *Attorney, Agent, or Firm* — Foley & Lardner LLP

(57) ABSTRACT

Preparations including FSH, for example recombinant FSH, for use in the treatment of infertility in patients having high AMH and low bodyweight.

19 Claims, 1 Drawing Sheet

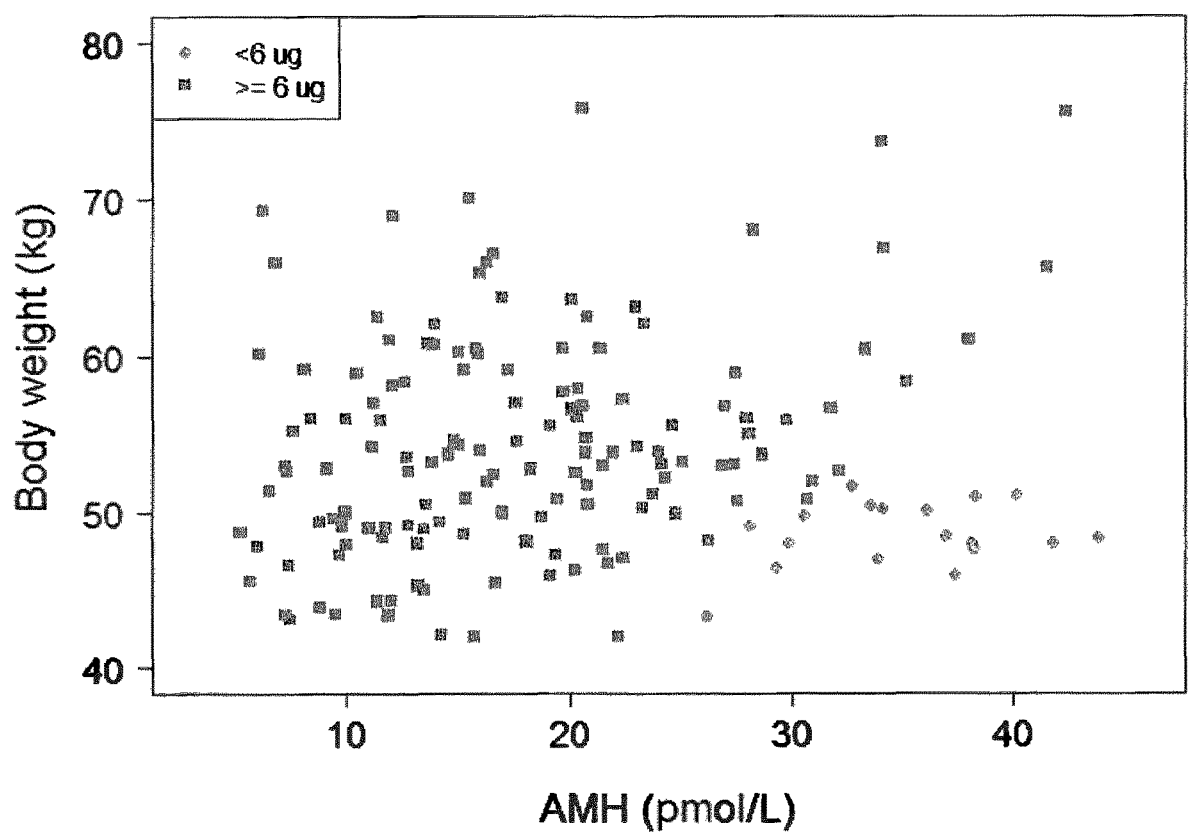

RECOMBINANT FSH COMPOSITION FOR CONTROLLED OVARIAN STIMULATION

CROSS-REFERENCE TO RELATED APPLICATIONS

The present application is the U.S. National Stage of International Application No. PCT/EP2018/073442, filed Aug. 31, 2018, and claims priority to European Patent Application No. 17189119.5, filed Sep. 1, 2017.

The present invention relates to compositions and pharmaceutical products for the treatment of infertility.

Assisted reproductive technology (ART) techniques such as in vitro fertilisation (IVF) are well known. These ART techniques generally require a step of controlled ovarian stimulation (COS), in which a cohort of follicles is stimulated to full maturity. Standard COS regimens include administration of gonadotrophins, such as follicle stimulating hormone (FSH), alone or in combination with luteinising hormone (LH) activity to stimulate follicular development, normally with administration of a GnRH analogue prior to and/or during stimulation to prevent premature LH surge. The pharmaceutical compositions generally used for COS include recombinant follicle stimulating hormone (rFSH) including Rekovelle® and Gonal F, urinary derived FSH, recombinant FSH+LH preparations, urinary derived menotrophin [human menopausal gonadotrophin (hMG)] and highly purified human menopausal gonadotrophin (HP-hMG). IVF can be associated with a risk of ovarian hyperstimulation syndrome (OHSS), which can be life threatening in severe cases.

The ability to predict the response potential of women to controlled ovarian stimulation (COS) may allow the development of individualised COS protocols. Such individualised protocols could, for example, reduce the risk of OHSS in women predicted to have an excessive response to stimulation, and/or improve pregnancy outcomes in women classed as poor responders. The serum concentration of anti-Müllerian hormone (AMH) is now established as a reliable marker of ovarian reserve. Decreasing levels of AMH are correlated with reduced ovarian response to gonadotrophins during COS. Further, high levels of AMH are a good predictor of excessive ovarian response, and an indicator of risk of OHSS.

In a preliminary study of women under 35 years old undergoing ART, the CONSORT dosing algorithm (incorporating basal FSH, BMI, age and AFC) was used to predict the optimal FSH starting dose for COS in women at risk of developing OHSS (Olivennes et. al., 2009). Individualising the dose led to adequate oocyte yield and good pregnancy rate. However, there were high rates of cancellations in the low dose group (75 IU FSH) due to inadequate response, and OHSS did occur in a significant proportion of the patients.

There is therefore a need for individualised COS protocols which provide adequate response to stimulation, and/or decreased risk of OHSS.

As indicated above, standard COS protocols may include administration of FSH. FSH is naturally secreted by the anterior pituitary gland and functions to support follicular development and ovulation. FSH comprises a 92 amino acid alpha sub-unit, also common to the other glycoprotein hormones LH and CG, and a 111 amino acid beta sub-unit unique to FSH that confers the biological specificity of the hormone (Pierce and Parsons, 1981). Each sub-unit is post translationally modified by the addition of complex carbohydrate residues. Both subunits carry 2 sites for N-linked glycan attachment, the alpha sub-unit at amino acids 52 and 78 and the beta sub-unit at amino acid residues 7 and 24 (Rathnam and Saxena, 1975, Saxena and Rathnam, 1976). FSH is thus glycosylated to about 30% by mass (Dias and Van Roey. 2001. Fox et al. 2001).

FSH purified from post-menopausal human urine has been used for many years in infertility treatment; both to promote ovulation in natural reproduction and to provide oocytes for assisted reproduction technologies. Until recently, the only approved recombinant FSH (rFSH) products for ovarian stimulation, such as follitropin alfa (GONAL-F, Merck Serono/EMD Serono) and follitropin beta (PUREGON/FOLLISTIM, MSD/Schering-Plough), were derived from a Chinese Hamster Ovary (CHO) cell line.

There is considerable heterogeneity associated with FSH preparations which relates to differences in the amounts of various isoforms present. Individual FSH isoforms exhibit identical amino acid sequences but differ in the extent to which they are post-translationally modified; particular isoforms are characterised by heterogeneity of the carbohydrate branch structures and differing amounts of sialic acid (a terminal sugar) incorporation, both of which appear to influence the specific isoform bioactivity.

Glycosylation of natural FSH is highly complex. The glycans in naturally derived pituitary FSH can contain a wide range of structures that can include combinations of mono-, bi-, tri- and tetra-antennary glycans (Pierce and Parsons, 1981. Ryan et al., 1987. Baenziger and Green, 1988). The glycans can carry further modifications: core fucosylation, bisecting glucosamine, chains extended with acetyl lactosamine, partial or complete sialylation, sialylation with $\alpha 2,3$ and $\alpha 2,6$ linkages, and sulphated galactosamine substituted for galactose (Dalpathado et al., 2006). Furthermore, there are differences between the distributions of glycan structures at the individual glycosylation sites. A comparable level of glycan complexity has been found in FSH derived from the serum of individuals and from the urine of post-menopausal women (Wide et al., 2007).

The glycosylation of recombinant FSH products reflects the range of glycosyl-transferases present in the host cell line. Commercially available rFSH products derived from engineered Chinese hamster ovary cells (CHO cells) have a more limited range of glycan modifications than those found on the natural products. Examples of the reduced glycan heterogeneity found in CHO cell derived rFSH include a lack of bisecting glucosamine and a reduced content of core fucosylation and acetyl lactosamine extensions (Hard et al., 1990). In addition, CHO cells are only able to add sialic acid using the $\alpha 2,3$ linkage (Kagawa et al, 1988, Takeuchi et al, 1988, Svensson et al., 1990); CHO cell derived rFSH only includes $\alpha 2,3$-linked sialic acid and does not include $\alpha 2,6$-linked sialic acid.

Thus CHO cell derived FSH is different from naturally produced FSH (e.g. human pituitary/serum/urinary FSH) which contains glycans with a mixture of $\alpha 2,3$ and $\alpha 2,6$-linked sialic acid, with a predominance of the former.

The present applicants have developed a human cell line derived recombinant FSH which is the subject of International Patent Application No. PCT/GB2009/000978, published as WO2009/127826A. Recombinant FSH with a mixture of both $\alpha 2,3$ and $\alpha 2,6$-linked sialic acid was made by engineering a human cell line to express both rFSH and $\alpha 2,3$ sialyltransferase. The expressed product is highly acidic and carries a mix of both $\alpha 2,3$- and $\alpha 2,6$-linked sialic acids; the latter provided by the endogenous sialyl transferase activity. It was found that the type of sialic acid linkage, $\alpha 2,3$- or $\alpha 2,6$-, can have a dramatic influence on biological clearance of FSH. Recombinant FSH with a mixture of both $\alpha 2,3$ and $\alpha 2,6$-linked sialic acid has two advantages over rFSH expressed in conventional CHO cells: first the material is more highly sialylated due to the combined activities of the two sialyltransferases; and secondly the material more closely resembles the natural FSH. This is likely to be more biologically appropriate compared to CHO cell derived recombinant products that have produce only α2,3 linked sialic acid (Kagawa et al, 1988, Takeuchi et al, 1988, Svensson et al., 1990) and have decreased sialic acid content (Ulloa-Aguirre et al. 1995., Andersen et al. 2004).

The amino acid sequence of the human cell line derived recombinant FSH which is the subject of International Patent Application No. PCT/GB2009/000978, published as WO2009/127826A, is the native sequence and is identical to natural human FSH and existing CHO-derived rFSH products. However, the present applicants have found that human derived recombinant FSH products (i.e. recombinant FSH produced or expressed in a human cell line e.g. made by engineering a human cell line) which have a mixture of both α2,3 and α2,6-linked sialic acid may be particularly effective when utilised in (e.g. individualised) COS protocols.

On 13 Dec. 2016, the European Commission (EC) granted marketing authorisation for REKOVELLE® (follitropin delta, also known as FE999049), a human cell line derived recombinant follicle stimulating hormone (human rFSH), for use in controlled ovarian stimulation for the development of multiple follicles in women undergoing assisted reproductive technologies (ART), such as an in vitro fertilisation (IVF) or intracytoplasmic sperm injection (ICSI) cycle. REKOVELLE® is the first rFSH to be derived from a human cell line. The REKOVELLE® (follitropin delta) product is produced by the methods disclosed in International Patent Application No. PCT/GB2009/000978.

Two randomised, controlled, assessor-blind, parallel groups, multi-centre phase 2 anti-Müllerian hormone (AMH)-stratified trials were conducted in IVF/ICSI patients, one in Europe and one in Japan, with the purpose of determining the dose-response relationship of FE 999049 and the number of oocytes retrieved. In both trials, randomisation was stratified according to AMH levels at screening; low AMH (5.0-14.9 pmol/L) or high AMH (15.0-44.9 pmol/L). In the European dose-response phase 2 trial, five doses of FE 999049 ranging from 5.2 μg/day to 12.1 μg/day were investigated and a reference group of an approved rFSH product (GONAL-F, 150 IU/day) was also included. In the Japanese dose-response phase 2 trial, three doses of FE 999049 (6 μg/day, 9 μg/day and 12 μg/day) were investigated and a standard therapy of the approved rFSH product (FOLLISTIM, 150 IU/day) was also included. At present, follitropin beta (FOLLISTIM) is the only medicinal product approved in Japan for controlled ovarian stimulation in IVF/ICSI cycles.

In the European and the Japanese phase 2 trials, the daily dose was fixed throughout the stimulation period. In both trials, a statistically significant dose response relationship for FE 999049 with respect to the number of oocytes retrieved was observed for the overall population and for each AMH randomisation stratum. Acceptable pregnancy rates were achieved with all FE 999049 doses. Furthermore, the observed FE 999049 dose-response profile was similar in the European trial and in the Japanese trial.

This work enabled the development of individualised COS protocols for dosing the REKOVELLE® (follitropin delta, FE999049) product.

The applicants have found that it is generally necessary to retrieve in the region of nine oocytes in order to enable selection of two high quality oocytes for transfer.

The applicants have found that for subjects having low AMH (AMH<15 pmol/L per litre) a reasonably high dose of follitropin delta is required (for example 12 μg) to achieve this. At this dose, 8 to 14 oocytes will be retrieved from 60% of subjects with low AMH. This is an unexpected and significant improvement over treatment of subjects with low AMH treated with 150 IU Gonal-f, where 8 to 14 oocytes are retrieved from only 33% of subjects. The applicants have found that there is no need to adjust this dose according to the bodyweight of the patient.

However, 60% of the population (and 80% of women under 30 treated for infertility) have high AMH (that is, AMH of ≥15 pmol/L). For these subjects it is generally fairly straightforward to retrieve a mean of 9 to 11 oocytes; the problem with stimulation protocols is the risk of OHSS. The applicants have found that in patients dosed at low doses of follitropin delta there is a relationship between oocytes retrieved and body weight of the subject. This means that there may be a risk associated with treatment with a fixed dose of FSH (which is usual in the art). The present applicants have established a relationship between dose of FSH and AMH level and weight of the subject which provides an improved safety profile (reduced risk of OHSS) with acceptable or improved oocyte retrieval compared to the known treatment protocols.

The posology of REKOVELLE is individualised for each patient and aims to obtain an ovarian response which is associated with a favourable safety/efficacy profile, i.e. aims to achieve an adequate number of oocytes retrieved and reduce the interventions to prevent ovarian hyperstimulation syndrome (OHSS). REKOVELLE is dosed in micrograms.

For the first treatment cycle, the individual daily dose will be determined on the basis of the woman's serum anti-Müllerian hormone (AMH) concentration and her body weight. The dose should be based on a recent determination of AMH (i.e. within the last 12 months) measured by the following diagnostic test from Roche: ELECSYS AMH Plus immunoassay. The individual daily dose is to be maintained throughout the stimulation period.

For women with AMH<15 pmol/L the daily dose of REKOVELLE is 12 micrograms, irrespective of body weight.

For women with AMH≥15 pmol/L the daily dose of REKOVELLE decreases from 0.19 to 0.10 micrograms/kg by increasing AMH concentration (Table 1, below).

The dose is to be rounded off to the nearest 0.33 micrograms to match the dosing scale on the injection pen. The maximum daily dose for the first treatment cycle is 12 micrograms. For calculation of the REKOVELLE dose, the body weight is to be measured without shoes and overcoat just prior to start of stimulation.

TABLE A

| | Dosing regimen | | | | | | | | | | |
|---|---|---|---|---|---|---|---|---|---|---|---|
| AMH (pmol/L) | <15 | 15-16 | 17 | 18 | 19-20 | 21-22 | 23-24 | 25-27 | 28-32 | 33-39 | ≥40 |
| Fixed daily dose of REKOVELLE | 12.0 mcg | 0.19 mcg/kg | 0.18 mcg/kg | 0.17 mcg/kg | 0.16 mcg/kg | 0.15 mcg/kg | 0.14 mcg/kg | 0.13 mcg/kg | 0.12 mcg/kg | 0.11 mcg/kg | 0.10 mcg/kg | mcg: micrograms

The AMH concentration is to be expressed in pmol/L and is to be rounded off to the nearest integer. If the AMH concentration is in ng/mL, the concentration should be converted to pmol/L by multiplying with 7.14 (ng/mL× 7.14=pmol/L) before use.

Treatment with REKOVELLE should be initiated day 2 or 3 after start of menstrual bleeding, and continue until adequate follicular development (≥3 follicles≥17 mm) has been achieved, which on average is by the ninth day of treatment (range 5 to 20 days). A single injection of 250 micrograms recombinant human chorionic gonadotropin (hCG) or 5,000 IU hCG is administered to induce final follicular maturation. In patients with excessive follicular development (of ≥25 follicles≥12 mm), treatment with REKOVELLE should be stopped and triggering of final follicular maturation with hCG should not be performed.

For subsequent treatment cycles, the daily dose of REKOVELLE should be maintained or modified according to the patient's ovarian response in the previous cycle. If the patient had adequate ovarian response in the previous cycle without developing OHSS, the same daily dose should be used. In case of ovarian hypo-response in the previous cycle, the daily dose in the subsequent cycle should be increased by 25% or 50%, according to the extent of response observed. In case of ovarian hyperresponse in the previous cycle, the daily dose in the subsequent cycle should be decreased by 20% or 33%, according to the extent of response observed. In patients who developed OHSS or were at risk of OHSS in a previous cycle, the daily dose for the subsequent cycle is 33% lower than the dose the cycle where OHSS or risk of OHSS occurred. The maximum daily dose is 24 micrograms.

The efficacy and safety of the FE 999049 individualised dosing regimen based on the woman's serum AMH and body weight has been confirmed in a large phase 3 trial, ESTHER-1 (Evidence based Stimulation Trial with Human rFSH in Europe and Rest of World), conducted in 11 countries including Europe, North America and Latin America. The ESTHER-1 trial was conducted in 1,326 IVF/ICSI patients who were randomised 1:1 to controlled ovarian stimulation with one of the following treatments: 1) FE 999049 in its individualised dosing regimen with the daily dose fixed throughout simulation, or 2) an approved CHO-derived rFSH product (follitropin alfa, GONAL-F) at a standard starting dose of 150 IU/day followed by dose adjustments based on the subject's follicular response during stimulation. FE 999049 in its individualised dosing regimen was demonstrated to be non-inferior to follitropin alfa with respect to ongoing pregnancy rate (30.7% versus 31.6%) and ongoing implantation rate (35.2% versus 35.8%). For the overall population, there was no statistically significant difference between treatment groups in terms of number of oocytes retrieved, with an average of 10.0 for FE 999049 and 10.4 for follitropin alfa. Nevertheless, the individualised FE 999049 dosing regimen in comparison to follitropin alfa led to statistically significantly more oocytes retrieved among patients with AMH<15 pmol/L (population at risk of hyporesponse) with an average of 8.0 versus 7.0 and statistically significantly fewer oocytes among patients with AMH≥15 pmol/L (population at risk of hyperresponse) with an average of 11.6 versus 13.3. The immediate clinical relevance of this shift in ovarian response with FE 999049 therapy was realised as statistically significantly fewer patients with extreme ovarian response compared to follitropin alfa, i.e. <4 oocytes among patients with AMH<15 pmol/L (12% versus 18%) and ≥15 or ≥20 oocytes among patients with AMH≥15 pmol/L (28% versus 35%, and 10% versus 16%). The percentage of patients with an appropriate ovarian response, defined for FE 999049 as 8-14 oocytes, was reached by statistically significantly more patients treated with FE 999049 compared to follitropin alfa, i.e. 43% versus 38%, despite implementation of dose adjustments during stimulation for 37% of the patients in the follitropin alfa group in contrast to the fixed-dose individualised dosing regimen for FE 999049. A statistically significantly lower total gonadotropin dose in the FE 999049 group compared to the CHO-derived rFSH product group was observed with an average of 90 μg and 104 μg, respectively.

The most serious risk associated with gonadotropin treatment is ovarian hyperstimulation syndrome (OHSS). Overall, in the ESTHER-1 phase 3 trials, OHSS and/or preventive interventions of early OHSS occurred in 4.4% of the FE 999049 cycles and 6.5% of the follitropin alfa cycles. Moderate/severe OHSS and/or preventive interventions for early OHSS were observed at an incidence of 3.3% and 5.6% of the treatment cycles with FE 999049 and follitropin alfa, respectively.

Previous studies have reported OHSS rates in Japanese patients between 5% and 28.3%. In the FE 999049 phase 2 trial in Japan, the incidence of early moderate/severe OHSS was 19.5% for subjects in the FOLLISTIM group. Despite the variation in the OHSS incidence reporting, the high OHSS incidence in Japanese IVF/ICSI patients illustrates a clear need in Japan for a treatment option with a safer OHSS profile. Based on more than 1,300 cycles in the ESTHER-1 phase 3 trial, the individualised dosing regimen of FE 999049 was associated with a statistically significant reduction in the proportion of subjects with early OHSS and/or preventive interventions for early OHSS in comparison to the standard regimen of CHO-derived rFSH product, with an incidence of 4.7% in the FE 999049 group and 6.2% in the follitropin alfa group.

In many Asian populations (for example Japan, China, South Korea and India), many women have a low body weight, compared to women in the US and Western Europe. There is therefore a risk that administering a fixed dose, suitable for the general population in Europe, to Asian/Japanese patients, could lead to these lighter patients receiving a dose of FSH which is overly high in terms of dose/kg body weight. This in turn could lead to risk of over-response and OHSS in these patients. The traditional "fixed dose" FSH protocols may be a factor in some high reported OHSS rates in Japan.

The dose protocol set out in Table A goes some way to mitigating this risk because patients are dosed by bodyweight. However, very low doses of gonadotropins are potentially associated with inadequate follicular recruitment and poor ovarian response. There is therefore a risk that dosing according to the Table A protocol might lead to very light patients with high AMH receiving a dose of FSH which may be sub-optimal from an efficacy perspective. There is therefore a need for effective dosing of lighter patients (weight<60 kg) with high AMH while reducing risk of overstimulation and OHSS in these patients (who may be more prone to this risk because they have high AMH and low bodyweight).

The present applicants identified patients in the Japanese phase 2 trial mentioned above (see also Example 2 below) who (based on AMH and body weight) would have received<6 μg FE 999049 according to the individualised FE 999049 dosing regimen set out in Table A, but actually received either 6 μg FE 999049 or 150 IU FOLLISTIM as per randomisation. This was only a very limited number of patients (5 patients in the 6 μg FE 999049 group, and 3 patients in the 150 IU FOLLISTIM group). Surprisingly, ovarian response of 15 oocytes or more was not observed in any of the 5 patients in the 6 µg FE 999049 group but in 2 of 3 patients (66.7%) in the 150 IU FOLLISTIM group. Also surprisingly, excessive follicular development requiring triggering with GnRH agonist was not observed in any of the 5 patients in the 6 µg FE 999049 group but in 1 of 3 patients (33.3%) in the 150 IU FOLLISTIM group. Early OHSS was reported for 1 of 5 patients (20.0%) in the 6 µg FE 999049 group and for 1 of 3 patients (33.3%) in the 150 IU FOLLISTIM group. These data support the safe and efficacious use of 6 µg FE 999049 in Japanese IVF/ICSI patients, including those patients with body weight<60 kg and AMH≥15 pmol/L.

The applicants surprisingly found that it is possible to specify a minimum dose of 6 µg to account for the lower body weight in the Japanese population, with the intention of avoiding underdosing of Japanese patients with low body weight, and thereby maintain efficacy in these patients, while avoiding side effects such as OHSS. It will be appreciated that this technical effect applies to any Asian population, or indeed any population which includes patients with low bodyweight and high AMH irrespective of the patient's ethnic background.

According to the present invention in a first aspect there is provided a composition (e.g. a pharmaceutical composition) for use in the treatment of infertility in a patient (e.g. a female patient) having AMH≥15 pmol/L (for example AMH≥16 pmol/L, for example AMH≥19 pmol/L, for example AMH≥26 pmol/L, for example AMH≥28 pmol/L, for example AMH≥40 pmol/L) and bodyweight<60 kg, the composition comprising a daily dose of, or a daily dose equivalent to, 6 to 8 µg recombinant FSH. Preferably, the composition comprises a daily dose of 6 to 8 µg recombinant FSH. More preferably, the composition comprises a daily dose of 6 µg recombinant FSH.

The treatment of infertility may include a step (or steps) of determining the serum AMH level and bodyweight of the patient. The treatment of infertility may include a step of administering the dose to the patient having the defined serum AMH level and bodyweight. For example, the treatment of infertility may include a step (or steps) of determining the serum AMH level and bodyweight of the patient, and a step of administering the dose to the patient having AMH 15 pmol/L (for example AMH≥16 pmol/L, for example AMH≥19 pmol/L, for example AMH≥26 pmol/L, for example AMH≥28 pmol/L, for example AMH≥40 pmol/L) and bodyweight<60 kg [e.g. bodyweight<55 kg, for example<52 kg, for example<50 kg, for example<45 kg].

The step of determining the serum AMH level of the patient may take place up to twelve months before the dose is first administered to the patient. Preferably the serum AMH level of the patient is determined (measured) by the ELECSYS AMH Plus immunoassay (available from Roche, of Switzerland, see www.roche.com). The step of determining the bodyweight of the patient may take place just before (e.g. 0 to 2 days before) the dose is first administered to the patient. The step of determining the bodyweight of the patient may use weighing scales, as are well known.

The composition (e.g. pharmaceutical composition) may be for use for treatment of infertility in a patient having bodyweight<59 kg, for example<56 kg, for example<55 kg, for example<52 kg, for example<50 kg, for example<45 kg, for example<42 kg, for example<31.5 kg. The composition (e.g. pharmaceutical composition) may be for use for treatment of infertility in a patient having bodyweight from 40 to 59.9 kg, for example for treatment of infertility in a patient having bodyweight from 45 to 55 kg. The composition may be for use for treatment of infertility in a patient having AMH≥16 pmol/L, for example AMH≥19 pmol/L, for example AMH≥26 pmol/L, for example AMH≥28 pmol/L, for example AMH≥30 pmol/L, for example AMH≥40 pmol/L.

Preferably, the composition (e.g. pharmaceutical composition) is for use for treatment of infertility in a patient having bodyweight<52 kg (for example 50 kg, for example<45 kg) and having AMH≥26 pmol/L (for example AMH≥28 pmol/L, for example AMH≥30 pmol/L, for example AMH≥40 pmol/L). In this example the treatment of infertility may include a step of determining the serum AMH level and bodyweight of the patient, and a step of administering the dose to a patient having AMH≥26 pmol/L and bodyweight<52 kg.

According to the present invention in a further aspect there is provided a composition (e.g. a pharmaceutical composition) for use in the treatment of infertility in a patient (e.g. a female patient) identified (prior to treatment) as having AMH≥15 pmol/L (for example AMH≥16 pmol/L, for example AMH≥19 pmol/L, for example AMH≥26 pmol/L, for example AMH≥28 pmol/L, for example AMH≥40 pmol/L) and identified (prior to treatment) as having bodyweight<60 kg, the composition comprising a daily dose of, or a daily dose equivalent to, 6 to 8 µg recombinant FSH. Preferably, the composition comprises a daily dose of 6 to 8 µg recombinant FSH. More preferably, the composition comprises a daily dose of 6 µg recombinant FSH.

The treatment of infertility may include a step of identifying the patient (prior to treatment) based on the serum AMH level and bodyweight of the patient. The treatment of infertility may include a step of administering the dose to the patient identified as having the defined serum AMH level and bodyweight. For example, the treatment of infertility may include a step of identifying the patient (prior to treatment) based on the serum AMH level and bodyweight of the patient, and a step of administering the dose to the patient identified (prior to treatment) as having AMH≥15 pmol/L (for example AMH≥16 pmol/L, for example AMH≥19 pmol/L, for example AMH≥26 pmol/L, for example AMH≥28 pmol/L, for example AMH≥40 pmol/L) and identified (prior to treatment) as having bodyweight<60 kg [e.g. bodyweight<55 kg, for example<52 kg, for example<50 kg, for example<45 kg].

The step of identifying the patient (prior to treatment) based on the serum AMH level and bodyweight of the patient may take place just before (e.g. 0 to 2 days before) the dose is first administered to the patient. The step of identifying the patient may be based on a serum AMH level determined previously (e.g. a serum AMH level determined up to twelve months before the dose is first administered to the patient). Preferably the serum AMH level of the patient is determined (measured) by the ELECSYS AMH Plus immunoassay (available from Roche, of Switzerland, see www.roche.com). The step of identifying the patient may be based on a bodyweight of the patient determined just before (e.g. 0 to 2 days before) the dose is first administered to the patient. The step of determining the bodyweight of the patient may use weighing scales, as are well known.

The composition (e.g. pharmaceutical composition) may be for use for treatment of infertility in a patient identified (prior to treatment) as having bodyweight<59 kg, for example<56 kg, for example<55 kg, for example<52 kg, for example<50 kg, for example<45 kg, for example<42 kg, for example<31.5 kg. The composition (e.g. pharmaceutical composition) may be for use for treatment of infertility in a patient identified (prior to treatment) as having bodyweight from 40 to 59.9 kg, for example for treatment of infertility in a patient having bodyweight from 45 to 55 kg. The composition may be for use for treatment of infertility in a patient identified (prior to treatment) as having AMH≥16 pmol/L, for example AMH≥19 pmol/L, for example AMH≥26 pmol/L, for example AMH≥28 pmol/L, for example AMH≥30 pmol/L, for example AMH≥40 pmol/L.

Preferably, the composition (e.g. pharmaceutical composition) is for use for treatment of infertility in a patient identified (prior to treatment) as having bodyweight<52 kg (for example<50 kg, for example<45 kg) and identified (prior to treatment) as having AMH≥26 pmol/L (for example AMH≥28 pmol/L, for example AMH≥30 pmol/L, for example AMH≥40 pmol/L). In this example the treatment of infertility may include a step of identifying the patient (prior to treatment) based on the serum AMH level and bodyweight of the patient, and a step of administering the dose to the patient identified (prior to treatment) as having AMH≥26 pmol/L, and identified (prior to treatment) as having bodyweight<52 kg.

Preferably the FSH is a recombinant FSH (rFSH). Preferably the rFSH (e.g. human cell line derived recombinant FSH) includes α2,3- and α2,6-sialylation. The FSH (rFSH) for use according to the invention may have 1% to 99% of the total sialylation being α2,3-sialylation. The FSH (rFSH) according to the invention may have 1% to 99% of the total sialylation being α2,6-sialylation. Preferably, 80 to 95%, for example 80 to 90%, for example 82 to 89%, for example 85 to 89% of the total sialylation is α2,3-sialylation. Preferably 5 to 20%, for example 10 to 20%, for example 11 to 18%, for example 11 to 15%, of the total sialylation is α2,6-sialylation. By sialylation it is meant the amount of sialic residues present on the FSH carbohydrate structures. α2,3-sialylation means sialylation at the 2,3 position (as is well known in the art) and α2,6 sialylation at the 2,6 position (also well known in the art). Thus "% of the total sialylation may be α 2,3 sialylation" refers to the % of the total number of sialic acid residues present in the FSH which are sialylated in the 2,3 position. The term "% of the total sialylation being α2,6-sialylation" refers to the % of the total number of sialic acid residues present in the FSH which are sialylated in the 2,6 position. The rFSH may be present as a single isoform or as a mixture of isoforms.

The composition may be for use for treatment of infertility in an Asian patient (e.g. Japanese, Chinese, Korean, Indian patient, for example a patient of Han, Yamato or Korean ethnicity).

According to the present invention in a further aspect there is provided a medicament for treatment of infertility in an Asian (e.g. Japanese, Chinese, Korean, Indian) patient comprising follicle stimulating hormone (FSH), preferably recombinant FSH; wherein the medicament is administered to an Asian (e.g. Japanese, Chinese, Korean, Indian) patient identified (prior to treatment) as having serum AMH level of ≥15 pmol/L (for example AMH≥16 pmol/L, for example AMH≥19 pmol/L, for example AMH≥28 pmol/L) and identified (prior to treatment) as having bodyweight less than 60 kg; and wherein the medicament is administered at a daily dose of, or daily dose equivalent to, 6 to 8 μg recombinant FSH. Preferably, the daily dose is 6 to 8 μg recombinant FSH. More preferably, the daily dose is 6 μg recombinant FSH.

The treatment of infertility may include a step of identifying the patient (prior to treatment) based on the serum AMH level and bodyweight of the patient. The treatment of infertility may include a step of administering the dose to the patient identified as having the defined serum AMH level and bodyweight. For example, the treatment of infertility may include a step of identifying the patient (prior to treatment) based on the serum AMH level and bodyweight of the patient, and a step of administering the dose to the patient identified (prior to treatment) as having AMH≥15 pmol/L (for example AMH≥16 pmol/L, for example AMH≥19 pmol/L, for example AMH≥26 pmol/L, for example AMH≥28 pmol/L, for example AMH≥40 pmol/L) and identified (prior to treatment) as having bodyweight<60 kg [e.g. bodyweight<55 kg, for example<52 kg, for example<50 kg, for example<45 kg].

The step of identifying the patient (prior to treatment) based on the serum AMH level and bodyweight of the patient may take place just before (e.g. 0 to 2 days before) the dose is first administered to the patient. The step of identifying the patient may be based on a serum AMH level determined previously (e.g. a serum AMH level determined up to twelve months before the dose is first administered to the patient). Preferably the serum AMH level of the patient is determined (measured) by the ELECSYS AMH Plus immunoassay (available from Roche, of Switzerland, see www.roche.com). The step of identifying the patient may be based on a bodyweight of the patient determined just before (e.g. 0 to 2 days before) the dose is first administered to the patient. The step of determining the bodyweight of the patient may use weighing scales, as are well known.

Herein, "day one of treatment", also referred to as "day one of stimulation", refers to the first day that the dose of (e.g. recombinant) FSH is administered to the patient. Day one of treatment (stimulation) may take place on day 1, 2 or 3, preferably day 2 or day 3, of the patient's menstrual cycle. In other words, day one of treatment (stimulation) may be one, two or three days, preferably two or three days, after the patient commences menstrual bleeding, as is well known in the art.

The dose of FSH starts on day one of treatment and may continue for two to twenty days, for example continue for 2, 3, 4, 5, 6, 7, 8, 9, 10, 11, 12, 13, 14, 15, 16, 17, 18, 19, or 20 days. The dose of FSH starts on day one of treatment and may continue for seven to thirteen days, for example nine to thirteen days, for example 10 to 13 days, for example 10 to 11 days. The dose of FSH may be administered at a dose equivalent to the daily doses mentioned above. For example the composition may be for administration at a dose of 18 μg FSH every three days (e.g. for administration on days 1, 4, 7 and so on).

The composition (e.g. pharmaceutical composition) or medicament may be administered after pre-treatment of the patient with a (different) pharmaceutical composition which suppresses endogenous gonadotropin production prior to day one of the treatment with FSH (e.g. after the subject has been (pre-)treated with a steroid, a GnRH agonist, a GnRH antagonist etc.). Herein, the term "pre-treated" or "pre-treatment" refers to administration of the pharmaceutical composition which suppresses endogenous gonadotropin production prior to day one of the treatment with FSH and hCG. This is well known in the art. Thus, the composition (e.g. pharmaceutical composition) or medicament may be for administration 12 to 16, e.g. 13 to 15, e.g. 14 days after administration of (e.g. after initiation of administration of, e.g. after initiation of daily administration of) a GnRH agonist (e.g. Synarel, Lupron, Decapeptyl). The product may be for administration with a GnRH agonist.

In other examples, the composition (e.g. pharmaceutical composition) or medicament may be for administration prior to administration of a GnRH antagonist (e.g. ganirelix, cetrorelix), for example for administration five or six days prior to administration of a GnRH antagonist. The product may be for administration with a GnRH antagonist.

Preferably the composition (e.g. pharmaceutical composition) or medicament is for administration prior to administration of a high (ovulatory) dose of hCG (for example 4,000 to 11,000 IU hCG, e.g. 5,000 IU hCG, 10,000 IU hCG etc.; or 150 to 350 microgram recombinant hCG, for example 250 microgram recombinant hCG) to induce final follicular maturation.

The doses above may be for treatment of infertility in the patient's (subject's) first stimulation protocol. It will be appreciated that for further stimulation cycles, the doses may be adjusted according to actual ovarian response in the first cycle.

The applicants have devised "individualised" COS protocols wherein specific doses of recombinant FSH having specific characteristics are used to treat patients based on their specific AMH levels, thereby increasing the likelihood of adequate response to stimulation (e.g. in patients having a low response potential), and/or decreased risk of OHSS (e.g. in patients classed as high or excessive responders).

The serum level of AMH may be determined (e.g. measured) by any method known in the art. The serum AMH level may be measured using the AMH Gen-II enzyme linked immunosorbent assay, a kit (Beckman Coulter, Inc., Webster, Tex.). This assay can detect AMH concentrations greater than 0.57 pmol/L with a minimum limit of quantitation of 1.1 pmol/L. The serum AMH level may be measured using the automated AMH ACCESS assay (Beckman Coulter, Inc., Webster, Tex.). Preferably, the serum AMH level is measured using the Elecsys® AMH assay from Roche Diagnostics. Other assays may be used.

Herein, serum AMH values are generally recited in terms of pmol/L. This may be converted to ng/mL using the conversion equation 1 ng/ml AMH=7.1 pmol/L AMH.

Herein the terms "patient" and "subject" are used interchangeably.

Herein the term "treatment of infertility" includes treatment of infertility by controlled ovarian stimulation (COS) or methods which include a step or stage of controlled ovarian stimulation (COS), for example Intra Uterine Insemination (IUI), in vitro fertilisation (IVF), or intracytoplasmic sperm injection (ICSI). The term "treatment of infertility" includes treatment of infertility by ovulation induction (OI) or by methods which include a step or stage of ovulation induction (OI). The term "treatment of infertility" includes treatment of infertility in a subject having tubal or unexplained infertility, including treatment of infertility in a subject having endometriosis, for example stage I or stage II endometriosis, and/or in a subject having anovulatory infertility, for example WHO type II anovulatory infertility, and/or in a subject with a partner with male factor infertility. The product (or composition) may be for (use in) the treatment of infertility (and/or for controlled ovarian stimulation) in a subject having endometriosis, for example in a subject having stage I or stage II endometriosis, as defined by The American Society for Reproductive Medicine (ASRM) classification system for the various stages of endometriosis, (stage IV most severe; stage I least severe) [American Society for Reproductive Medicine. Revised American Society for Reproductive Medicine classification of endometriosis: 1996. Fertil Steril 1997; 67,817 821.].

The composition or medicament may be for (use in) the treatment of infertility (and/or for controlled ovarian stimulation) in a subject having normal serum FSH level of 1 to 16 IU/L, for example 1 to 12 IU/L, in the early follicular phase.

The composition or medicament may be for (use in) the treatment of infertility (and/or for controlled ovarian stimulation) in a subject aged 18 to 42 years, for example 25 to 37 years. The product may be for (use in) the treatment of infertility (and/or for controlled ovarian stimulation) in a subject having BMI≥1 and BMI<35 kg/m², for example a subject having BMI≥18 and BMI<25 kg/m², for example a subject having BMI≥20 and BMI<25 kg/m².

The rFSH may be produced or expressed in a human cell line, for example a Per.C6 cell line, a HEK293 cell line, a HT1080 cell line etc. This may simplify (and render more efficient) the production method because manipulation and control of e.g. the cell growth medium to retain sialylation may be less critical than with known processes. The method may also be more efficient because there is little basic rFSH produced compared to production of known rFSH products; more acidic rFSH is produced and separation/removal of basic FSH is less problematic. The rFSH may be produced or expressed in a PER.C6® cell line, a PER.C6® derived cell line or a modified PER.C6® cell line. rFSH which is produced or expressed in a human cell line (e.g. PER.C6® cell line, HEK293 cell line, HT1080 cell line etc.) will include some α2,6-linked sialic acids (α2,6 sialylation) provided by endogenous sialyl transferase activity [of the cell line] and will include some α2,3-linked sialic acids (α2,3 sialylation) provided by endogenous sialyl transferase activity. The cell line may be modified using α2,3-sialyltransferase. The cell line may be modified using α2,6-sialyltransferase. Alternatively or additionally, the rFSH may include α2,6-linked sialic acids (α2,6 sialylation) provided by endogenous sialyl transferase activity [of the cell line]. Herein, the term "human derived recombinant FSH" means recombinant FSH which is produced or expressed in a human cell line (e.g. recombinant FSH made by engineering a human cell line).

The rFSH may be produced using α2,3- and/or α2,6-sialyltransferase. In an example, rFSH is produced using α2,3-sialyltransferase. The rFSH may include α2,6-linked sialic acids (α2,6 sialylation) provided by endogenous sialyl transferase activity.

The composition may be a pharmaceutical composition. The pharmaceutical composition is for the treatment of infertility. The treatment of infertility may comprise assisted reproductive technologies (ART), ovulation induction or intrauterine insemination (IUI). The pharmaceutical composition may be used, for example, in medical indications where known FSH preparations are used.

The composition or medicament can be formulated into well-known compositions for any route of drug administration, e.g. oral, rectal, parenteral, transdermal (e.g. patch technology), intravenous, intramuscular, subcutaneous, intrasusternal, intravaginal, intraperitoneal, local (powders, ointments or drops) or as a buccal or nasal spray. A typical composition comprises a pharmaceutically acceptable carrier, such as aqueous solution, non toxic excipients, including salts and preservatives, buffers and the like, as described in Remington's Pharmaceutical Sciences fifteenth edition (Matt Publishing Company, 1975), at pages 1405 to 1412 and 1461-87, and the national formulary XIV fourteenth edition (American Pharmaceutical Association, 1975), among others.

Examples of suitable aqueous and non-aqueous pharmaceutical carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. The compositions or medicaments of the present invention also can contain additives such as but not limited to preservatives, wetting agents, emulsifying agents, surfactants and dispersing agents. Antibacterial and antifungal agents can be included to prevent growth of microbes and includes, for example, m-cresol, benzyl alcohol, paraben, chlorobutanol, phenol, sorbic acid, and the like. If a preservative is included, benzyl alcohol, phenol and/or m-cresol are preferred; however, the preservative is by no means limited to these examples. Furthermore, it may be desirable to include isotonic agents such as sugars, sodium chloride, and the like.

The composition or medicament may further comprise a salt comprising a pharmaceutically acceptable alkali metal cation selected from the group consisting of $Na^+$- or $K^+$-salts, or a combination thereof. Preferably the salt is a $Na^+$-salt, for example NaCl or $Na_2SO_4$.

Preferably the composition or medicament comprises recombinant FSH and one or more of Polysorbate 20, L-methionine, phenol, disodium sulphate and sodium phosphate buffer.

In some cases, to effect prolonged action it is desirable to slow the absorption of FSH (and other active ingredients, if present) from subcutaneous or intramuscular injection. This can be accomplished by the use of a liquid suspension of crystalline or amorphous material with poor water solubility. The rate of absorption of FSH then depends upon its rate of dissolution which, in turn, can depend upon crystal size and crystalline form. Alternatively, delayed absorption of a parenterally administered FSH combination form is accomplished by dissolving or suspending the FSH combination in an oil vehicle. Injectable depot forms can be made by forming microencapsule matrices of the FSH (and other agents, if present) in biodegradable polymers such as polylactide-polyglycolide. Depending upon the ratio of FSH to polymer and the nature of the particular polymer employed, the rate of FSH release can be controlled. Examples of other biodegradable polymers include polyvinylpyrrolidone, poly (orthoesters), poly(anhydrides) etc. Depot injectable formulations are also prepared by entrapping the FSH in liposomes or microemulsions which are compatible with body tissues.

Injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use. Injectable formulations can be supplied in any suitable container, e.g. vial, pre-filled syringe, injection cartridges, and the like.

The composition or medicament may be formulated for single use or for multiple use (multiple dose). If the composition or medicament is formulated for multiple use, it is preferred that a preservative is included. If a preservative is included, benzyl alcohol, phenol and/or m-cresol are preferred; however, the preservative is by no means limited to these examples. The single use or multiple use formulated composition or medicament may further comprise a salt comprising a pharmaceutically acceptable alkali metal cation selected from the group consisting of $Na^+$- or $K^+$-salts, or a combination thereof. Preferably the salt is a $Na^+$-salt, for example NaCl or $Na_2SO_4$.

The composition or medicament may be included in a container such as a vial, prefilled cartridge (e.g. for single administration or multiple use) or an injection device such as a "pen" for e.g. administration of multiple doses.

The composition or medicament may be a formulation (e.g. injectable formulation) including FSH (optionally with hCG, LH, LH activity etc.) The LH activity, if present, may originate from LH or human chorionic gonadotropin, hCG. If there is more than one active ingredient (i.e. FSH and e.g. hCG or LH) these may be suitable for administration separately or together. If administered separately, administration can be sequential. The composition or medicament can be supplied in any appropriate package. For example, a composition or medicament can include a number of containers (e.g. pre-filled syringes or vials) containing either FSH or hCG, or a combination (or combination) of both FSH and hCG. The hCG may be recombinant hCG or urinary hCG. If the composition or medicament includes a number of containers (e.g. pre-filled syringes or vials) containing FSH, e.g. recombinant FSH, each container may include the same amount of FSH. One or more containers may include different amounts of FSH. The syringes or vials may be packaged in a blister package or other means to maintain sterility. Any composition or medicament can optionally contain instructions for using the FSH (and e.g. hCG if present) formulations. The pH and exact concentration of the various components of the pharmaceutical composition are adjusted in accordance with routine practice in this field. See GOODMAN and GILMAN's THE PHARMACOLOGICAL BASIS FOR THERAPEUTICES, $7^{th}$ ed. In a preferred embodiment, the composition or medicament of the invention are supplied as compositions for parenteral administration. General methods for the preparation of the parenteral formulations are known in the art and are described in REMINGTON; THE SCIENCE AND PRACTICE OF PHARMACY, supra, at pages 780-820. The parenteral compositions can be supplied in liquid formulation or as a solid which will be mixed with a sterile injectable medium just prior to administration. In an especially preferred embodiment, the parenteral compositions are supplied in dosage unit form for ease of administration and uniformity of dosage.

According to the present invention in a further aspect there is provided a method of treatment of infertility comprising: a step of administering a daily dose of, or a daily dose equivalent to, 6 to 8 µg recombinant FSH, to a patient (e.g. a female patient) having AMH 15 pmol/L (for example AMH≥16 pmol/L, for example AMH≥19 pmol/L, for example AMH≥26 pmol/L, for example AMH≥28 pmol/L, for example AMH≥40 pmol/L) and bodyweight<60 kg [e.g. bodyweight<55 kg, for example<52 kg, for example<50 kg, for example<45 kg, for example<42 kg, for example<31.5 kg]. Preferably, the daily dose is 6 to 8 µg recombinant FSH. More preferably, the daily dose is 6 µg recombinant FSH.

The method may include a step of determining the serum AMH level and bodyweight of the patient. The method may include a step of administering the dose to the patient having the defined serum AMH level and bodyweight. For example, the method may include a step of determining the serum AMH level and bodyweight of the patient, and a step of administering the dose to the patient having AMH≥15 pmol/L (for example AMH≥16 pmol/L, for example AMH 19 pmol/L, for example AMH≥26 pmol/L, for example AMH≥28 pmol/L, for example AMH≥40 pmol/L) and bodyweight<60 kg (e.g. bodyweight<55 kg, for example<52 kg, for example<50 kg, for example<45 kg, for example<42 kg, for example<31.5 kg).

According to the present invention in a further aspect there is provided a method of treatment of infertility comprising a step of administering a daily dose of, or a daily dose equivalent to, 6 to 8 µg recombinant FSH to a patient (e.g. a female patient) identified (prior to treatment) as having AMH≥15 pmol/L (for example AMH≥16 pmol/L, for example AMH≥19 pmol/L, for example AMH≥26 pmol/L, for example AMH≥28 pmol/L, for example AMH≥40 pmol/L) and identified (prior to treatment) as having bodyweight<60 kg (e.g. bodyweight<55 kg, for example<52 kg, for example<50 kg, for example<45 kg). Preferably, the daily dose is 6 to 8 µg recombinant FSH. More preferably, the daily dose is 6 µg recombinant FSH.

The method may include a step of identifying the patient (prior to treatment) based on the serum AMH level and bodyweight of the patient. The method may include a step of administering the dose to a patient identified as having the defined serum AMH level and bodyweight. For example, the method may include a step of identifying the patient (prior to treatment) based on the serum AMH level and bodyweight of the patient, and a step of administering the dose to the patient identified (prior to treatment) as having AMH≥15 pmol/L (for example AMH≥16 pmol/L, for example AMH≥19 pmol/L, for example AMH≥26 pmol/L, for example AMH≥28 pmol/L, for example AMH≥40 pmol/L) and identified (prior to treatment) as having bodyweight<60 kg [e.g. bodyweight<55 kg, for example<52 kg, for example<50 kg, for example<45 kg].

The method may be for use for treatment of infertility in an Asian (e.g. Japanese, Chinese, Korean, Indian) patient.

Preferably, the patient has (is identified as having) bodyweight<52 kg (for example<50 kg, for example<45 kg) and has (is identified as having) AMH≥26 pmol/L (for example AMH≥28 pmol/L, for example AMH≥30 pmol/L, for example AMH≥40 pmol/L).

Preferably the FSH is a recombinant FSH (rFSH). Preferably the rFSH (e.g. human cell line derived recombinant FSH) includes α2,3- and α2,6-sialylation. The FSH (rFSH) for use according to the invention may have 1% to 99% of the total sialylation being α2,3-sialylation. The FSH (rFSH) according to the invention may have 1% to 99% of the total sialylation being α2,6-sialylation. Preferably, 80 to 95%, for example 80 to 90%, for example 82 to 89%, for example 85 to 89% of the total sialylation is α2,3-sialylation. Preferably 5 to 20%, for example 10 to 20%, for example 11 to 18%, for example 11 to 15%, of the total sialylation is α2,6-sialylation. By sialylation it is meant the amount of sialic residues present on the FSH carbohydrate structures. α2,3-sialylation means sialylation at the 2,3 position (as is well known in the art) and α2,6 sialylation at the 2,6 position (also well known in the art). Thus "% of the total sialylation may be α2,3 sialylation" refers to the % of the total number of sialic acid residues present in the FSH which are sialylated in the 2,3 position. The term "% of the total sialylation being α2,6-sialylation" refers to the % of the total number of sialic acid residues present in the FSH which are sialylated in the 2,6 position. The rFSH may be present as a single isoform or as a mixture of isoforms.

According to the present invention in an aspect there is provided a composition for use in the treatment of infertility in a patient having AMH≥26 pmol/L and bodyweight<52 kg, the composition comprising a daily dose of 6 to 8 µg recombinant FSH. Preferably, the patient has (is identified as having) bodyweight<52 kg (for example<50 kg, for example<45 kg) and has (is identified as having) AMH≥26 pmol/L (for example AMH≥28 pmol/L, for example AMH≥30 pmol/L, for example AMH≥40 pmol/L).

According to the present invention in another aspect there is provided a composition for use in the treatment of infertility in a patient having AMH≥26 pmol/L and bodyweight<61 kg, the composition comprising a daily dose of, or a daily dose equivalent to, 6 to 8 µg recombinant FSH. Preferably, the patient has (is identified as having) bodyweight<52 kg (for example<50 kg, for example<45 kg) and has (is identified as having) AMH≥26 pmol/L (for example AMH 28 pmol/L, for example AMH≥30 pmol/L, for example AMH≥40 pmol/L).

DETAILED DESCRIPTION OF THE INVENTION

The present invention will now be described in more detail with reference to the following examples and FIG. 1 which presents the body weight and AMH of all patients in the Japanese Phase II clinical trial discussed in the retrospective analysis of Example 3, and indicates whether the dose protocol set out in Table A above would specify a dose of <6 µg Rekovelle® (diamonds) or ≥6 µg Rekovelle.

EXAMPLE 1—REKOVELLE

Rekovelle® is a recombinant FSH expressed in a PER.C6® cell line engineered by the methods disclosed in WO2013/020996 and WO2009/127826A.

The Marketing Authorisation holder for Rekovelle® is Ferring Pharmaceuticals NS of Kay Fiskers Plads 11, 2300 Copenhagen S, Denmark, and it is available in the UK from Ferring Pharmaceuticals of Drayton Hall, Church Road, West Drayton, UB7 7PS, UK The active substance in Rekovelle® is follitropin delta (FE999049). Rekovelle is highly sialylated and includes α2,3- and α2,6-sialylation, with about 85% to 90% of the total sialylation being α2,3-sialylation and about 10% to 15% of the total sialylation being α2,6-sialylation.

REKOVELLE is a clear and colourless solution for injection (injection). It is available in packs of 1 cartridge and 3 pen injection needles. Each multidose cartridge contains 12 micrograms of follitropin delta in 0.36 millilitre of solution. One millilitre of solution contains 33.3 micrograms of follitropin delta in each millilitre of solution. The other ingredients are phenol, polysorbate 20, L-methionine, sodium sulphate decahydrate, disodium phosphate dodecahydrate, concentrated phosphoric acid, sodium hydroxide and water for injections.

EXAMPLE 2—A RANDOMISED, ASSESSOR-BLIND, (AMH)-STRATIFIED, DOSE RESPONSE TRIAL IN JAPANESE IVF/ICSI PATIENTS UNDERGOING CONTROLLED OVARIAN STIMULATION WITH FOLLITROPIN DELTA

A randomised, controlled, assessor-blind, parallel groups, multi-centre phase 2 anti-Müllerian hormone (AMH)-stratified trials was conducted in IVF/ICSI patients in Japan, with the purpose of determining the dose-response relationship of FE 999049 and the number of oocytes retrieved. Randomisation was stratified according to AMH levels at screening; low AMH (5.0-14.9 pmol/L) or high AMH (15.0-44.9 pmol/L).

There were 158 patients, 20 to 39 years (mean age 33.7 years) undergoing COS with three dose levels of FE 999049, follitropin delta (Ferring Pharmaceuticals). The doses of FE 999049 were 6 µg/day, 9 µg/day and 12 µg/day and a standard therapy of the approved rFSH product (FOLLISTIM, MSD, 150 IU/day) was also included as control. At present, follitropin beta (FOLLISTIM) is the only medicinal product approved in Japan for controlled ovarian stimulation in IVF/ICSI cycles.

Patients were randomised to fixed doses of 6 μg/day, 9 μg/day and 12 μg/day FE 999049 (n=117) or 150 IU follitropin beta (n=41). Randomisation was stratified according to AMH level [low AMH=5.0-14.9 pmol/L; high AMH=15.0 to 44.9 pmol/L; Elecsys AMH, Roche Diagnostics). Gonadotropin ws initiated on day 2-3 of the menstrual cycle. Ganrelix 0.25 mg/day added from day 6 of stimulation and triggering of final follicular maturation was done on the day when≥3 follicles with a diameter≥17 mm are observed. OHSS was assessed using Golan's classification.

The daily dose was fixed throughout the stimulation period. A statistically significant dose response relationship for FE 999049 with respect to the number of oocytes retrieved was observed for the overall population and for each AMH randomisation stratum. Acceptable pregnancy rates were achieved with all FE 999049 doses.

Patients were not dosed by body weight in this trial and no patient received a dose below 6 μg/day FE 999049. No patient in this trial was identified prior to treatment by combination of AMH and bodyweight.

EXAMPLE 3 RETRO-ANALYSIS OF PHASE II TRIAL

In many Asian countries (for example Japan, China, South Korea and India), many women have a low body weight, compared to women in the US and Western Europe. There is therefore a risk that administering a fixed dose, suitable for the general population in Europe, to Asian/Japanese patients, could lead to low body-weight patients receiving a dose of FSH which is high in terms of dose/kg body weight. This in turn could lead to risk of over-response and OHSS in these patients. The traditional "fixed dose" FSH protocols may be a factor in some high reported OHSS rates in Japanese studies.

The dose protocol set out in Table A above goes some way to mitigating this risk because patients are dosed by bodyweight. However, very low doses of gonadotropins are potentially associated with inadequate follicular recruitment and poor ovarian response. There is therefore a risk that dosing according to the Table A protocol might lead to very light patients with high AMH receiving a dose of FSH which may be sub-optimal from an efficacy perspective. There is therefore a need for effective dosing of lighter patients (weight<60 kg) with high AMH while reducing risk of overstimulation and OHSS in these patients (who may be more prone to this risk because they have high AMH and low bodyweight).

Overall in the Japanese phase 2 trial, there were no safety concerns with the FE 999049 dose of 6 μg. The safety profile of patients in the Japanese phase 2 trial who had a body weight<60 kg has been investigated retrospectively. As context to the observations in the 6 μg FE 999049 group, the data from the reference therapy group with FOLLISTIM are also displayed. Table 1 displays safety parameters relevant to ovarian response.

TABLE 1

Comparison of Ovarian Response Safety Parameters for Subjects <60 kg exposed to 6 μg FE 999049 or 150 IU FOLLISTIM - overall

| | FE 999049 6 ug (N = 29) | | FOLLISTIM 150 IU (N = 33) | |
|---|---|---|---|---|
| | n | % | n | % |
| Early OHSS | 4 | 13.8% | 8 | 24.2% |
| Early Moderate/Severe OHSS | 3 | 10.3% | 7 | 21.2% |
| GnRH agonist triggering | | | 1 | 3.0% |
| 15-19 oocytes retrieved | 1 | 3.4% | 5 | 15.2% |
| >=20 oocytes retrieved | | | 2 | 6.1% |

Among patients with a body weight<60 kg, the total number of patients with early OHSS was 4 (13.8%) in the 6 μg FE 999049 group and 8 (24.2%) in the 150 IU FOLLISTIM group. Early moderate/severe OHSS was reported for 3 (10.3%) patients and 7 (21.2%) patients in the 6 μg FE 999049 and 150 IU FOLLISTIM groups, respectively. Furthermore, oocyte yield above the appropriate response of 8-14 oocytes was only observed in 1 (3.4%) patient in the 6 μg FE 999049 group in contrast to 7 (21.2%) patients in the 150 IU FOLLISTIM group. Excessive follicular development to the extent that GnRH agonist triggering was required was not observed in any patients in the 6 μg FE 999049 group, but did occur for 1 patient in the 150 IU FOLLISTIM group. Thus, the safety ovarian response profile in patients weighing<60 kg seems to be improved with 6 μg FE 999049 compared to 150 IU FOLLISTIM.

Table 1 covers all patients with body weight<60 kg, independent of AMH level. All patients with AMH<15 pmol/L will receive 12 μg FE 999049. The situation where a patient may have a calculated dose<6 μg but will receive 6 μg is therefore only applicable to patients with AMH≥15 pmol/L. Data on patients in the Japanese phase 2 trial who had body weight<60 kg and AMH≥15 pmol/L are presented in Table 2.

TABLE 2

Comparison of Ovarian Response Safety Parameters for Subjects <60 kg exposed to 6 μg FE 999049 or 150 IU FOLLISTIM - High AMH Stratum

| | FE 999049 6 ug (N = 18) | | FOLLISTIM 150 IU (N = 22) | |
|---|---|---|---|---|
| | n | % | n | % |
| Early OHSS | 4 | 22.2% | 7 | 31.8% |
| Early Moderate/Severe OHSS | 3 | 16.7% | 6 | 27.3% |
| GnRH agonist triggering | | | 1 | 4.5% |
| 15-19 oocytes retrieved | 1 | 5.6% | 4 | 18.2% |
| >=20 oocytes retrieved | | | 2 | 9.1% |

Among the patients with a body weight<60 kg and AMH≥15 pmol/L, the total number of patients with early OHSS was 4 (22.2%) in the 6 μg FE 999049 group and 7 (31.8%) in the 150 IU FOLLISTIM group. Moderate/severe OHSS was the most common severity among the early OHSS cases and was reported for 3 (16.7%) patients in the 6 μg FE 999049 group and 6 (27.3%) patients in the 150 IU FOLLISTIM group. While only 1 (5.6%) patient in the 6 μg FE 999049 group had 15-19 oocytes retrieved, this was the case of 4 (18.2%) patients in the 150 IU FOLLISTIM group where additionally 2 (9.1%) patients had ≥20 oocytes. Triggering with GnRH agonist due to excessive follicular development was not needed in the 6 µg FE 999049 group but was needed for 1 patient in the 150 IU FOLLISTIM group. Thus, controlled ovarian stimulation with 6 µg FE 999049 in patients weighing<60 kg and with AMH≥15 pmol/L was associated with less risk of early OHSS and less risk of excessive ovarian response than controlled ovarian stimulation with 150 IU FOLLISTIM.

Concerning the adverse event profile in patients with a body weight<60 kg, the frequency of adverse events judged by the investigator to be related to the drug used for controlled ovarian stimulation was 20.7% in the 6 µg FE 999049 group and 33.3% in the 150 IU FOLLISTIM group. Among the patients with body weight<60 kg and AMH≥15 pmol/L, the frequency of related adverse events was 27.8% in the 6 µg FE 999049 group and 36.4% in the 150 IU FOLLISTIM group.

From an efficacy perspective, the clinical pregnancy rate per cycle with transfer in patients with body weight<60 kg was 40.0% in the 6 µg FE 999049 group and 21.7% in the standard therapy group. For patients with body weight<60 kg and AMH≥15 pmol/L, the clinical pregnancy rate per cycle with transfer was 38.5% and 20.0% in the 6 µg FE 999049 and standard therapy groups, respectively.

Finally, Ferring identified the patients in the Japanese phase 2 trial who based on AMH and body weight would have received<6 µg FE 999049 according to the individualised FE 999049 dosing regimen (Table A above), but in this trial received either 6 µg FE 999049 or 150 IU FOLLISTIM as per randomisation. This was only a very limited number of patients (5 patients in the 6 µg FE 999049 group, and 3 patients in the 150 IU FOLLISTIM group), but the ovarian response safety data were in line with those presented earlier. Ovarian response of 15 oocytes or more was not observed in any of the 5 patients in the 6 µg FE 999049 group but in 2 of 3 patients (66.7%) in the 150 IU FOLLISTIM group. Excessive follicular development requiring triggering with GnRH agonist was not observed in any of the 5 patients in the 6 µg FE 999049 group but in 1 of 3 patients (33.3%) in the 150 IU FOLLISTIM group. Early OHSS was reported for 1 of 5 patients (20.0%) in the 6 µg FE 999049 group and for 1 of 3 patients (33.3%) in the 150 IU FOLLISTIM group.

In other words, the applicants surprisingly found that it is possible to specify a minimum dose of 6 µg to account for the lower body weight in the Japanese population, with the intention of avoiding underdosing of Japanese patients with low body weight, and thereby maintain efficacy in these patients, while avoiding side effects such as OHSS.

In addition to the safety and efficacy data with 6 µg FE 999049 in the Japanese phase 2 trial supporting the appropriateness of this dose, simulations have been conducted using the dose-response model that has been estimated from the Japanese phase 2 trial. The purpose of these simulations is to evaluate the expected difference in the number of oocytes with the proposed dosing regimen with 6 µg as the lowest dose compared to a dosing regimen with doses allowed to be <6 µg. Based on the body weight and AMH levels of all 158 randomised patients in the Japanese phase 2 trial, 18 (11%) would receive with the proposed dosing regimen a dose of 6 µg instead of a calculated dose<6 µg. All of these patients had a body weight below 52 kg and an AMH exceeding 26 pmol/L, as illustrated in FIG. 1, which presents the body weight and AMH of all patients in the trial. FIG. 1 shows these 18 patients with small diamonds (rather than squares) to the bottom right of the FIG.

In the 18 patients with a calculated dose<6 µg, the mean calculated dose is 5.33 µg and the proposed dosing regimen amounts thus to a 13% higher mean dose compared to the regimen without a minimum (mean dose 6.0 µg instead of 5.33 µg).

The ovarian response is expected to be beneficially influenced by implementing 6 µg as the minimum dose. In patients with a calculated dose<6 µg, more patients are anticipated to achieve the target of 8-14 oocytes retrieved with the proposed dosing regimen where 6 µg is the minimum dose (48.0% of patients, versus 44.8% with the regimen without a minimum dose), as shown in Table 3.

TABLE 3

Predicted outcome in Japanese patients with calculated dose <6 µg FE 999049

| Treatment outcome for FE 999049 | No minimum dose established | Minimum dose of 6 µg | Difference |
| --- | --- | --- | --- |
| Patients with 8-14 oocytes retrieved | 44.8% | 48.0% | +3.2% |

Thus, in addition to the observed data from the Japanese phase 2 trial, model predictions of the ovarian response with the proposed dosing regimen further support the appropriateness of a minimum dose of 6 µg.

In conclusion, the proposed FE 999049 dosing regimen, including the implementation of 6 µg as the minimum dose, is safe and efficacious, and is proposing this for the phase 3 trial in Japan. Phase 3 data on Japanese patients with a calculated dose<6 µg will be analysed specifically for the purpose of PMDA review to support the efficacy and safety of 6 µg FE 999049 in these patients.

EXAMPLE 10—PHASE 3 CLINICAL TRIAL IN JAPAN

Methodology

This will be a randomised, assessor-blind, controlled, parallel groups, multicentre trial assessing the efficacy and safety of FE 999049 in its individualised dosing regimen when used in first cycle Japanese patients aged 20-40 years undergoing controlled ovarian stimulation for IVF/ICSI following a gonadotropin-releasing hormone (GnRH) antagonist protocol. The trial has been designed to demonstrate non-inferiority of FE 999049 versus an rFSH product approved in Japan, i.e. FOLLISTIM, with respect to number of oocytes retrieved.

Subjects will be screened within 60 days prior to start of stimulation for compliance with the inclusion and exclusion criteria. On day 2-3 of the menstrual cycle, subjects will be randomised in a 1:1 ratio to controlled ovarian stimulation with FE 999049 or FOLLISTIM. Randomisation will be stratified by centre and according to AMH levels at screening (<15 pmol/L and ≥15 pmol/L).

Subjects randomised to FE 999049 will have their individual FE 999049 dose determined on the basis of their AMH level at screening and their body weight at start of stimulation (see below). The daily FE 999049 dose will be fixed throughout the stimulation period. For subjects with AMH<15 pmol/L, the daily FE 999049 dose is 12 µg, irrespective of body weight. For subjects with AMH≥15 pmol/L the daily FE 999049 dose is on a continuous scale ranging from 0.19 to 0.10 µg/kg, i.e. dependent on actual AMH and body weight. This is set out in the Table below. The minimum allowed daily FE 999049 dose is 6 µg and the maximum allowed daily FE 999049 dose is 12 µg. Subjects can be treated with FE 999049 for a maximum of 20 days, and coasting is not allowed.

For subjects randomised to FOLLISTIM, the dosing regimen is within labelling (see below). The starting dose of FOLLISTIM is 150 IU and fixed for the first five stimulation days after which it may be adjusted by 75 IU based on the individual response. The maximum daily FOLLISTIM dose allowed is 375 IU. Subjects can be treated with FOLLISTIM for a maximum of 20 days, and coasting is not allowed.

During stimulation, subjects will be monitored by transvaginal ultrasound on stimulation day 1 and 6 and hereafter at least every second day. When 3 follicles of ≥15 mm are observed, visits must be performed daily. To prevent a premature luteinising hormone (LH) surge, a GnRH antagonist will be initiated on stimulation day 6 at a daily dose of 0.25 mg and continued throughout the stimulation period. Triggering of final follicular maturation will be done with 5,000 IU urinary human chorionic gonadotropin (hCG) on the day when≥3 follicles with a diameter≥17 mm are observed. In case of excessive follicular development, defined as ≥25 follicles with a diameter≥12 mm, the cycle should be cancelled (note: in case of 25-35 follicles with a diameter mm, a GnRH agonist may be administered as triggering for final follicular maturation). In case of poor follicular development, defined as the investigator judging that ≥3 follicles with a diameter≥17 mm cannot be reached by day 20, the cycle is to be cancelled.

Oocyte retrieval will take place 36 h (±2 h) after triggering of final follicular maturation and the oocytes can be inseminated by IVF or ICSI. Fertilisation and embryo development will be assessed from oocyte retrieval to the day of transfer. One blastocyst of the best quality available will be transferred on day 5 after oocyte retrieval while remaining blastocysts may be cryopreserved. For subjects who underwent triggering of final follicular maturation with GnRH agonist, no transfer will take place and blastocysts may instead be cryopreserved on day 5. All cryopreserved blastocysts can be used by the subject after completion of the trial, in accordance with the declaration by Japan Society of Obstetrics and Gynaecology (JSOG).

Vaginal progesterone tablets (LUTINUS, Ferring Pharmaceuticals) 100 mg three times daily will be provided for luteal phase support from the day after oocyte retrieval until the day of the clinical pregnancy visit. Luteal phase support will only be provided to subjects planned to undergo transfer and can be terminated earlier in case of no transfer or a negative βhCG test. A βhCG test is performed 13-15 days after transfer followed by a transvaginal ultrasound 5-6 weeks after transfer to assess clinical and vital pregnancy.

Blood samples will be collected during the trial for the purpose of evaluating the endocrine profile as well as clinical chemistry and haematology parameters. Endocrine parameters are measured at screening, stimulation day 1, stimulation day 6 and end-of-stimulation. Clinical chemistry and haematology parameters are assessed at screening, end-of-stimulation and end-of-trial. Local tolerability of FE 999049 following subcutaneous administration will be assessed by the subjects three times daily: immediately, 30 minutes and 24 hours after the injection. The assessment of injection site reactions will be made throughout the stimulation period and recorded by the subjects in a diary.

If trial procedures and/or assessments are to be performed on Sundays, public holidays or outside the opening hours of the clinic, the procedures and/or assessments can be postponed to the upcoming weekday (maximum one day after original visit schedule) or cancelled, if appropriate.

As obligatory follow-up, pregnancy progress and outcome data will be gathered for subjects with a vital pregnancy. Data will be collected on ongoing pregnancy (10-11 weeks after transfer) and pregnancy outcome as well as neonatal health at birth and at 4 weeks after birth. The pregnancy follow-up does not include any interventions but only data collection. The pregnancy follow-up data will be based on reports obtained from the subject's gynaecologist/obstetrician and the subject's Maternal and Child Health Handbook. The data will be retrieved by the trial site, either via the subject's gynaecologist/obstetrician, the subject herself, or other sources, as applicable. Ferring intends to submit the J-NDA following completion of the main part of the trial (i.e. up to the clinical pregnancy visit), and to include the pregnancy follow-up data available at that time in the J-NDA. The pregnancy follow-up data can be submitted after completion.

Number of Subjects

Approximately 328 subjects will be randomised in a 1:1 ratio to FE 999049 and FOLLISTIM.

Criteria for Inclusion/Exclusion

Women eligible for IVF and/or ICSI treatment, undergoing their first IVF/ICSI cycle and diagnosed with tubal infertility, unexplained infertility, infertility related to endometriosis stage I/II or with partners diagnosed with male factor infertility, will be included in this trial. Subjects will be 20-40 years of age, with a body mass index (BMI) of 17.5-32.0 kg/m2.

Women with endometriosis stage III/IV, history of recurrent miscarriage or with contraindications to controlled ovarian stimulation with gonadotropins will be excluded from participation in this trial.

The complete list of inclusion and exclusion criteria is provided below.

Inclusion Criteria

1. Informed Consent Documents signed prior to any trial-related procedures.
2. In good physical and mental health.
3. Japanese females between the ages of 20 and 40 years. The subjects must be at least 20 years (including the 20th birthday) when they sign the Informed Consent Documents and no more than 40 years (up to the day before the 41st birthday) at the time of randomisation.
4. Infertile women diagnosed with tubal infertility, unexplained infertility, endometriosis stage I/II (defined by the revised American Society for Reproductive Medicine (ASRM) classification) or with partners diagnosed with male factor infertility, eligible for in vitro fertilisation (IVF) and/or intracytoplasmic sperm injection (ICSI) treatment using ejaculated sperm from male partner.
5. Infertility for at least 1 year before randomisation (not applicable in case of tubal or severe male factor infertility).
6. The trial cycle will be the subject's first controlled ovarian stimulation cycle for IVF/ICSI.
7. Regular menstrual cycles of 24-35 days (both inclusive), presumed to be ovulatory.
8. Hysterosalpingography, hysteroscopy, saline infusion sonography or transvaginal ultrasound documenting a uterus consistent with expected normal function (e.g. no evidence of clinically interfering uterine fibroids defined as submucous or intramural fibroids larger than 3 cm in diameter, no polyps and no congenital structural abnormalities which are associated with a reduced chance of pregnancy) within 1 year prior to screening. This also includes women who have been diagnosed with any of the above medical conditions but have had them surgically corrected within 1 year prior to screening.

9. Transvaginal ultrasound documenting presence and adequate visualisation of both ovaries, without evidence of significant abnormality (e.g. no endometrioma greater than 3 cm or enlarged ovaries which would contraindicate the use of gonadotropins) and fallopian tubes and surrounding tissue without evidence of significant abnormality (e.g. no hydrosalpinx) within 1 year prior to screening. Both ovaries must be accessible for oocyte retrieval.

10. Early follicular phase (cycle day 2-4) serum levels of FSH between 1 and 15 IU/L (results obtained within 3 months prior to screening).

11. Negative serum Hepatitis B Surface Antigen (HBsAg), Hepatitis C Virus (HCV) and Human Immunodeficiency Virus (HIV) antibody tests within 1 year prior to screening.

12. Body mass index (BMI) between 17.5 and 32.0 kg/m2 (both inclusive) at screening.

13. Willing to accept transfer of one blastocyst.

Exclusion Criteria

1. Known endometriosis stage III-IV (defined by the revised ASRM classification).

2. One or more follicles>10 mm (including cysts) observed on the transvaginal ultrasound prior to start of stimulation on stimulation day 1 (puncture of cysts prior randomisation is allowed).

3. Known history of recurrent miscarriage (defined as three consecutive losses after ultrasound confirmation of pregnancy (excl. ectopic pregnancy) and before week 24 of pregnancy).

4. Known abnormal karyotype of subject or of her partner. In case the sperm production is severely impaired (concentration<1 million/mL), normal karyotype, including no Y-chromosome microdeletion, must be documented.

5. Active arterial or venous thromboembolism or severe thrombophlebitis, or a history of these events.

6. Known *porphyria*.

7. Any known clinically significant systemic disease (e.g. insulin-dependent diabetes).

8. Known inherited or acquired thrombophilia disease.

9. Any known endocrine or metabolic abnormalities (pituitary, adrenal, pancreas, liver or kidney) which can compromise participation in the trial with the exception of controlled thyroid function disease.

10. Known presence of anti-FSH antibodies (based on the information available in the subject's medical records).

11. Known tumours of the ovary, breast, uterus, adrenal gland, pituitary or hypothalamus which would contraindicate the use of gonadotropins.

12. Any abnormal finding of clinical chemistry, haematology or vital signs at screening, which is judged clinically relevant by the investigator.

13. Known moderate or severe impairment of renal or hepatic function.

14. Currently breast-feeding.

15. Undiagnosed vaginal bleeding.

16. Known abnormal cervical cytology of clinical significance observed within 3 years prior to screening (unless the clinical significance has been resolved).

17. Findings from the laboratory analyses at screening which preclude gonadotropin stimulation.

18. Findings at the gynaecological examination at screening which preclude gonadotropin stimulation.

19. Findings at the gynaecological examination at screening which are associated with a reduced chance of pregnancy, e.g. congenital uterine abnormalities or retained intrauterine device.

20. Pregnancy (must be confirmed by negative urinary pregnancy tests at screening and prior to randomisation) or contraindication to pregnancy.

21. Known current active pelvic inflammatory disease.

22. Use of hormonal preparations (except for thyroid medication) or fertility modifiers during the last menstrual cycle before screening, including dehydroepiandrosterone (DHEA), metformin and cycle programming with oral contraceptives, progestogen or oestrogen preparations.

23. Known history of chemotherapy (except for gestational conditions) or radiotherapy.

24. Current or past (1 year prior to randomisation) abuse of alcohol or drugs, and/or current (last month) intake of more than 14 units of alcohol per week.

25. Current or past (3 months prior to randomisation) smoking habit of more than 10 cigarettes per day.

26. Hypersensitivity to any drug substance or excipients in the medicinal products used in the trial.

27. Hypersensitivity to any drug substance or excipients in a GnRH or any GnRH analogue/derivative. 28. Previous participation in the trial.

29. Current participation in another trial, including follow-up period.

30. Use of any non-registered investigational drugs during the last 3 months prior to screening.

On day 2-3 of the menstrual cycle, subjects will be randomised in a 1:1 ratio to treatment with either FE 999049 or FOLLISTIM, and controlled ovarian stimulation will be initiated.

FE 999049 Dosing Regimen

Subjects randomised to FE 999049 will have their individual dose determined on the basis of their AMH level at screening and their body weight at randomisation. For subjects with AMH<15 pmol/L the daily FE 999049 dose is 12 µg, irrespective of body weight. For subjects with AMH≥15 pmol/L the daily FE 999049 dose is on a continuous scale ranging from 0.19 to 0.10 µg/kg, i.e. dependent on actual AMH and body weight.

The daily FE 999049 dose will be fixed throughout the stimulation period. The minimum allowed daily FE 999049 dose is 6 µg. The maximum allowed daily FE 999049 dose is 12 µg. Dosing will continue until the criterion for triggering of final follicular maturation has been met. Subjects can be treated with FE 999049 for a maximum of 20 days. Coasting is not allowed.

The complete FE 999049 dosing regimen is tabulated in detail in the following Table:

| Treatment group | AMH concenteation (pmol/L) | Daily dose fixed throught stimulation | Minimum daily dose | Maximum daily dose |
|---|---|---|---|---|
| FE 999049 | <15 | 12 µg | — | 12 µg |
| | 15-16 | 0.19 µg/kg | 6 µg | 12 µg |
| | 17 | 0.18 µg/kg | 6 µg | 12 µg |
| | 18 | 0.17 µg/kg | 6 µg | 12 µg |
| | 19-20 | 0.16 µg/kg | 6 µg | 12 µg |
| | 21-22 | 0.15 µg/kg | 6 µg | 12 µg |
| | 23-24 | 0.14 µg/kg | 6 µg | 12 µg |
| | 25-27 | 0.13 µg/kg | 6 µg | 12 µg |
| | 28-32 | 0.12 µg/kg | 6 µg | 12 µg |
| | 33-39 | 0.11 µg/kg | 6 µg | 12 µg |
| | ≥40 | 0.10 µg/kg | 6 µg | 12 µg |

AMH concentration will be rounded off to integers.
Subjects can be treated for a maximum of 20 days.

The FE 999049 preparation is administered as a single daily subcutaneous injection in the abdomen. The dose must not be split into two injections. To minimise local injection site reactions, it is advisable to change injection site regularly.

The first FE 999049 injection will take place at the clinic and will be performed either by the trial medication delegate or the subject under supervision by the trial medication delegate. Subsequent injections can be done at home or at the clinic. The trial medication delegate will give the subject instructions for how to administer FE 999049.

Calculation of the FE 999049 Dose and Setting the Dose on the FE 999049 Pre-Filled Pen The subject's serum AMH concentration will be available from the blood sample taken at screening and analysed by a central laboratory using Elecsys® AMH assay from Roche Diagnostics. The AMH concentration will be provided from the central laboratory directly to the eCRF. The subject's body weight will be measured at randomisation using a calibrated scale and performed without shoes and overcoat. The body weight result will be entered into the eCRF. The FE 999049 dosing algorithm has been programmed in the eCRF, which calculates the FE 999049 dose based on the subject's AMH and body weight.

The FE 999049 pre-filled injection pen is intended for subcutaneous administration of FE 999049. It is a non-sterile needle-based disposable device with integrated non-replaceable 3 mL cartridge containing the liquid FE 999049 drug product. Each cartridge holds multiple doses, the size of which are adjustable by the user. It is possible to set doses from 0.33 µg to 20.0 µg in increments of 0.33 µg. The FE 999049 pre-filled injection pen has a dosing scale numbered from 0 to 20 µg. Each number is separated by two lines, each line representing 0.33 µg. The pre-filled injection pen can be set to deliver doses rounded to the nearest 0.33 µg. Rounding off of the calculated dose may be needed, as in this example of a subject weighing 75.0 kg with an AMH level of 35 pmol/L for whom the calculated dose is 8.25 µg (0.11 µg/kg*75.0 kg), which will then be rounded to 8.33 µg, i.e. 8 µg+1 line on the pen. The eCRF will provide the calculated dose in an output that matches the numbers and lines on the pre-filled injection pen; i.e. any rounding off will be done automatically prior to providing the subject's calculated dose.

The trial medication delegate will be instructed and trained in the correct use of the pre-filled injection pen, so that correct instructions can be provided to the subject.

5.1.2 FOLLISTIM Dosing Regimen

For subjects randomised to FOLLISTIM, the dosing regimen is within labelling. The starting dose of FOLLISTIM is 150 IU and fixed for the first five stimulation days, after which it may be adjusted by 75 IU based on the individual response. The maximum daily FOLLISTIM dose allowed is 375 IU. Dosing will continue until the criterion for triggering of final follicular maturation has been met. Subjects can be treated with FOLLISTIM for a maximum of 20 days. Coasting is not allowed. The FOLLISTIM dosing regimen is shown in detail in the following Table.

| Treatment group | Starting dose stimulation day 1-5 | Daily dose stimulation day 6 and onwards | Minimum daily dose | Maximum daily dose |
|---|---|---|---|---|
| FOLLISTIM | 150 IU | Adjustments of 75 IU allowed according to the individual response. | 75 IU | 375 IU |

Subjects can be treated for a maximum of 20 days.

REFERENCES

Andersen C Y, Westergaard L G, and van Wely M. (2004). FSH isoform composition of commercial gonadotrophin preparations: a neglected aspect? Reprod Biomed Online. 9(2), 231-236.

Arey B J, Stevis P E, Deecher D C, Shen E S, Frail D E, Negro-Vilar A, and Lopez F J. (1997) Induction of promiscuous G protein coupling of the follicle-stimulating hormone (FSH) receptor: a novel mechanism for transducing pleiotropic actions of FSH isoforms. Mol Endocrinol. 11(5), 517-526.

Baenziger J U and Green E D. (1988). Pituitary glycoprotein hormone oligosaccharides: structure, synthesis and function of the asparagine-linked oligosaccharides on lutropin, follitropin and thyrotropin. Biochim Biophys Acta. 947 (2), 287-306.

Bassett R M, and Driebergen R. (2005). Continued improvements in the quality and consistency of follitropin alfa, recombinant human FSH. Reprod Biomed Online. 10(2), 169-177.

Damián-Matsumura P, Zaga V, Maldonado A, Sánchez-Hernández C, Timossi C, and Ulloa-Aguirre A. (1999). Oestrogens regulate pituitary alpha2,3-sialyltransferase messenger ribonucleic acid levels in the female rat. J Mol Endocrinol. 23(2), 153-165.

D'Antonio M., Borrelli F., Datola A., Bucci R., Mascia M., Polletta P., Piscitelli D., and Papoian R. (1999) Biological characterization of recombinant human follicle stimulating hormone isoforms. Human Reproduction 14, 1160-1167

Dalpathado D S, Irungu J, Go E P, Butnev V Y, Norton K, Bousfield G R, and Desaire H. (2006). Comparative glycomics of the glycoprotein follicle stimulating hormone: glycopeptide analysis of isolates from two mammalian species. Biochemistry. 45(28), 8665-8673. No copy Dias J A, Van Roey P. (2001). Structural biology of human follitropin and its receptor. Arch Med Res. 32(6), 510-519

Fiddes, J. C. and Goodman, H. M. (1979) Isolation, cloning and sequence analysis of the cDNA for the alpha-subunit of human chorionic gonadotropin. Nature, 281, 351-356.

Flack, M. R., Bennet, A. P., Froehlich, J. Anasti, J N and Nisula, B. (1994). Increased biological activity due to basic isoforms in recombinant human follicle-stimulating hormone produced in a human cell line. J. Clin. Endocrinol. Metab., 79, 756-760

Fox K M, Dias J A, and Van Roey P. (2001). Three-dimensional structure of human follicle-stimulating hormone. Mol Endocrinol. 15(3), 378-89

Grabenhorst E, Hoffmann A, Nimtz M, Zettlmeissl G, and Conradt H S. (1995). Construction of stable BHK-21 cells coexpressing human secretory glycoproteins and human Gal(beta 1-4)GlcNAc-R alpha 2,6-sialyltransferase alpha 2,6-linked NeuAc is preferentially attached to the Gal (beta 1-4)GlcNAc(beta 1-2)Man(alpha 1-3)-branch of diantennary oligosaccharides from secreted recombinant beta-trace protein. Eur J Biochem. 232(3), 718-25.

Green E D and Baenziger J U. (1988). Asparagine-linked oligosaccharides on lutropin, follitropin, and thyrotropin. II. Distributions of sulfated and sialylated oligosaccharides on bovine, ovine, and human pituitary glycoprotein hormones. J Biol Chem. 263(1), 36-44.

Grundmann, U., Nerlich, C., Rein, T. and Zettlmeissl, G. (1990). Complete cDNA sequence encoding human beta-galactoside alpha-2,6-sialyltransferase. G Nucleic Acids Res. 18 (3), 667

Howles, C. M. (1996). Genetic engineering of human FSH (Gonal-F). Hum Reprod. Update, 2, 172-191.

Kagawa Y, Takasaki S, Utsumi J, Hosoi K, Shimizu H, Kochibe N, and Kobata A. (1988). Comparative study of the asparagine-linked sugar chains of natural human interferon-beta 1 and recombinant human interferon-beta 1 produced by three different mammalian cells. J Biol Chem. 263(33), 17508-17515.

Keene, J. L., Matzuk, M. M., Otani, T., Fauser, B, C, J, M., Galway, A. B., Hsueh, A. J. W. and Boime, I. (1989). Expression of Biologically active Human Follitropin in Chinese Hamster Ovary Cells. The Journal of Biological Chemistry, 264(9), 4769-4775.

Kitagawa, H. and Paulson, J. C (1994) Cloning of a novel alpha 2,3-sialyltransferase that sialylates glycoprotein and glycolipid carbohydrate groups. J. Biol. Chem. 269(2), 1394-1401.

Lee E U, Roth J, and Paulson J C (1989) Alteration of terminal glycosylation sequences on N-linked oligosaccharides of Chinese hamster ovary cells by expression of beta-galactoside alpha 2,6-sialyltransferase. J Biol Chem. 264(23), 13848-13855.

de Leeuw, R., Mulders, J., Voortman, G. Rombout, F. Damm, J. and Kloosterboer, L. (1996) Structure-function relationship of recombinant follicle stimulating hormone (Puregon). Mol. Hum. Reprod., 2, 361-369.

Lowry O H, Rosebrough N J, Farr A L, Randall R J. (1951) Protein measurement with the Folin phenol reagent. J Biol Chem. 193(1), 265-75.

Lowry, P J, McLean, C, Jones R L and Satgunasingam N. (1976) Purification of anterior pituitary and hypothalamic hormones Clin Pathol Suppl (Assoc Clin Pathol). 7, 16-21.

Olivennes F, Howles C M, Borini A, Germond M, Trew G, Wikland M, Zegers-Hochschild F, Saunders H (2009) Individualizing FSH dose for assisted reproduction using a novel algorithm: the CONSORT study. Reprod Biomed Online. 2009 February; 18(2):195-204.

Pierce J G, and Parsons T F (1981) Glycoprotein hormones: structure and function Annu Rev Biochem. 50 465-495.

Pricer W E Jr, and Ashwell G. (1971). The binding of desialylated glycoproteins by plasma membranes of rat liver. J Biol Chem. 246(15), 4825-33.

Rathnam P, and Saxena B B. (1975). Primary amino acid sequence of follicle-stimulating hormone from human pituitary glands. I. alpha subunit. J Biol Chem.; 250(17): 6735-6746.

Regoeczi E, Debanne M T, Hatton M C, and Koj A. (1978) Elimination of asialofetuin and asialoorosomucoid by the intact rat. Quantitative aspects of the hepatic clearance mechanism. Biochim Biophys Acta. 541(3), 372-84.

Royle L, Radcliffe C M, Dwek R A and Rudd P M (2006) Methods in Molecular Biology, ed I Brockhausen-Schutzbach (Humana Press), 347: Glycobiology protocols, 125-144.

Ryan R J, Keutmann H T, Charlesworth M C, McCormick D J, Milius R P, Calvo F O and Vutyavanich T.

(1987). Structure-function relationships of gonadotropins. Recent Prog Horm Res.; 43: 383-429.

Saxena B B and Rathnam P. (1976) Amino acid sequence of the beta subunit of follicle-stimulating hormone from human pituitary glands. J Biol Chem. 251(4), 993-1005

Steelman S L, and Pohley F M. (1953) Assay of the follicle stimulating hormone based on the augmentation with human chorionic gonadotropin. Endocrinology. 53(6), 604-616.

Steer C J, and Ashwell G. (1980) Studies on a mammalian hepatic binding protein specific for asialoglycoproteins. Evidence for receptor recycling in isolated rat hepatocytes. J Biol Chem. 255(7), 3008-13.

Svensson E C, Soreghan B, and Paulson J C. (1990) Organization of the beta-galactoside alpha 2,6-sialyltransferase gene. Evidence for the transcriptional regulation of terminal glycosylation. J Biol Chem. 265(34):20863-20868.

Takeuchi M, Takasaki S, Miyazaki H, Kato T, Hoshi S, Kochibe N, and Kobata A (1988). Comparative study of the asparagine-linked sugar chains of human erythropoietins purified from urine and the culture medium of recombinant Chinese hamster ovary cells. J Biol Chem. 263(8), 3657-3663.

Timossi C M, Barrios de Tomasi J, Zambrano E, González R, Ulloa-Aguirre A. (1998). A naturally occurring basically charged human follicle-stimulating hormone (FSH) variant inhibits FSH-induced androgen aromatization and tissue-type plasminogen activator enzyme activity in vitro. Neuroendocrinology. 67(3), 153-163.

Timossi C M, Barrios-de-Tomasi J, González-Suárez R, Arranz M C, Padmanabhan V, Conn P M, and Ulloa-Aguirre A. (2000). Differential effects of the charge variants of human follicle-stimulating hormone. J Endocrinol. 165(2), 193-205.

Ulloa-Aguirre, A., Espinoza, R., Damian-Matsumura, P. and Chappel, S. C. (1988) Immunological and biological potencies of the different molecular species of gonadotrophins. Hum. Reprod. 3, 491-501.

Ulloa-Aguirre, A., Cravioto, A., Damián-Matsumura, P. Jimenez, M, Zambrano, E and Diaz-Sanchez, V. (1992) Biological characterization of the naturally occurring analogues of intrapituitary human follicle stimulating hormone. Hum. Reprod. 7, 23-30.

Ulloa-Aguirre A, Midgley A R Jr, Beitins I Z, and Padmanabhan V. (1995). Follicle-stimulating isohormones: characterization and physiological relevance. Endocr Rev. 16(6), 765-787.

Ulloa-Aguirre A, Maldonado A, Damián-Matsumura P, and Timossi C (2001). Endocrine regulation of gonadotropin glycosylation. Arch Med Res. 32(6), 520-532.

Ulloa-Aguirre A, Timossi C, Barrios-de-Tomasi J, Maldonado A, and Nayudu P. (2003). Impact of carbohydrate heterogeneity in function of follicle-stimulating hormone: studies derived from in vitro and in vivo models. Biol Reprod. 69(2), 379-389.

Van Lenten L, and Ashwell G. (1972) The binding of desialylated glycoproteins by plasma membranes of rat liver. Development of a quantitative inhibition assay. J Biol Chem. 247(14), 4633-40.

Wide, L. and Albertsson-Wikland, K. (1990) Change in electrophoretic mobility of human follicle-stimulating hormone in serum after administration of gonadotropin-releasing hormone. J. Clin. Endocrinol. Metab. 70 271-276.

Wide, L. and Bakos, O. (1993). More basic forms of both human follicle-stimulating hormone and luteinizing hormone in serum at midcycle compared with the follicular or luteal phase. J. Clin. Endocrinol. Metab., 76 885-889.

Wide L, Naessén T, Sundström-Poromaa I, Eriksson K. (2007) Sulfonation and sialylation of gonadotropins in women during the menstrual cycle, after menopause, and with polycystic ovarian syndrome and in men. J Clin Endocrinol Metab.; 92(11), 4410-4417.

Zambrano E, Zariñán T, Olivares A, Barrios-de-Tomasi J, and Ulloa-Aguirre A. (1999). Receptor binding activity and in vitro biological activity of the human FSH charge isoforms as disclosed by heterologous and homologous assay systems: implications for the structure-function relationship of the FSH variants. Endocrine. 10(2), 113-121.

Zhang X, Lok S H, and Kon O L (1998) Stable expression of human alpha-2,6-sialyltransferase in Chinese hamster ovary cells: functional consequences for human erythropoietin expression and bioactivity. Biochim Biophys Acta. 1425(3), 441-452.

The invention claimed is:

1. A method of treating infertility in a female patient in need thereof, comprising identifying a female patient having a serum anti-Müllerian hormone (AMH) level≥26 pmol/L and a bodyweight<42 kg prior to treatment, and administering daily to the patient 0.18 ml of a solution of recombinant FSH in water with a concentration of 33.3 µg recombinant FSH per ml of water.

2. The method of claim 1, further comprising determining the patient's serum AMH level and bodyweight prior to treatment.

3. The method of claim 1, wherein the patient has a bodyweight<31.5 kg prior to treatment.

4. The method of claim 1, wherein the patient has a serum AMH level≥30 pmol/L prior to treatment.

5. The method of claim 1, wherein the patient for treatment of infertility is an Asian patient.

6. The method of claim 1, wherein the patient for treatment of infertility is a Japanese patient.

7. The method of claim 1, wherein the recombinant FSH includes α2,3- and α2,6 sialylation.

8. The method of claim 1, wherein the patient is in need of treatment of infertility by controlled ovarian stimulation.

9. The method of claim 1, wherein the 0.18 ml of the solution of recombinant FSH in water with a concentration of 33.3 µg recombinant FSH per ml of water is administered daily for from two to twenty days.

10. The method of claim 1, wherein the 0.18 ml of the solution of recombinant FSH in water with a concentration of 33.3 µg recombinant FSH per ml of water is administered by subcutaneous injection.

11. A method of treating infertility in a female patient in need thereof, comprising identifying a female patient having a serum anti-Mülllerian hormone (AMH) level≥40 pmol/L and a bodyweight<52 kg prior to treatment, and administering daily to the patient 0.18 ml of a solution of recombinant FSH in water with a concentration of 33.3 µg recombinant FSH per ml of water.

12. The method of claim 11, wherein the patient has a bodyweight<50 kg prior to treatment.

13. The method of claim 11, wherein the patient has a bodyweight<45 kg prior to treatment.

14. The method of claim 11, further comprising determining the patient's serum AMH level and bodyweight prior to treatment.

15. The method of claim 11, wherein the patient for treatment of infertility is an Asian patient.

16. The method of claim 11, wherein the recombinant FSH includes α2,3- and α2,6 sialylation.

17. The method of claim 11, wherein the patient is in need of treatment of infertility by controlled ovarian stimulation.

18. The method of claim 11, wherein the 0.18 ml of the solution of recombinant FSH in water with a concentration of 33.3 µg recombinant FSH per ml of water is administered daily for from two to twenty days.

19. The method of claim 11, wherein the 0.18 ml of the solution of recombinant FSH in water with a concentration of 33.3 µg recombinant FSH per ml of water is administered by subcutaneous injection.

* * * * *